United States Patent
Smith et al.

(10) Patent No.: US 9,797,856 B2
(45) Date of Patent: Oct. 24, 2017

(54) SYSTEM AND METHOD FOR THREAD PROTRUSION VERIFICATION

(71) Applicants: Jamie M. Smith, Keller, TX (US); Eric Grabow, Lake Oswego, OR (US); Douglas Howard McKay, Grand Prairie, TX (US); Matthew Timothy McKee, Willow Park, TX (US); Russell Miller, Danbury, TX (US); David Andrew Nicholson, Jr., Wichita, KS (US)

(72) Inventors: Jamie M. Smith, Keller, TX (US); Eric Grabow, Lake Oswego, OR (US); Douglas Howard McKay, Grand Prairie, TX (US); Matthew Timothy McKee, Willow Park, TX (US); Russell Miller, Danbury, TX (US); David Andrew Nicholson, Jr., Wichita, KS (US)

(73) Assignee: Lockheed Martin Corporation, Bethesda, MD (US)

( * ) Notice: Subject to any disclaimer, the term of this patent is extended or adjusted under 35 U.S.C. 154(b) by 149 days.

(21) Appl. No.: 14/798,135

(22) Filed: Jul. 13, 2015

(65) Prior Publication Data
US 2017/0016841 A1    Jan. 19, 2017

(51) Int. Cl.
*G08B 21/00*   (2006.01)
*G01N 27/20*   (2006.01)
(Continued)

(52) U.S. Cl.
CPC ............. *G01N 27/20* (2013.01); *G01B 7/004* (2013.01); *G01B 7/02* (2013.01); *G01B 7/042* (2013.01); *G01D 5/25* (2013.01); *G08B 21/18* (2013.01)

(58) Field of Classification Search
CPC .......... G08B 13/06; B65D 90/00; G01B 3/22; G01B 3/20; B25B 23/14
USPC .................. 340/568.4, 568.1, 686.4; 81/429; 33/645, 784; 439/416, 503, 729, 431, 2, 439/67, 213, 763, 415
See application file for complete search history.

(56) References Cited

U.S. PATENT DOCUMENTS 2,562,831 A * 7/1951 Stone ...................... B25B 23/14
                                                        116/DIG. 35
4,162,639 A * 7/1979 Gill ......................... B25B 23/14
                                                        81/429

(Continued)

FOREIGN PATENT DOCUMENTS

| JP | H11 153401 A | 6/1999 |
| JP | 2001 255103 A | 9/2001 |
| WO | WO 2014/027194 A1 | 2/2014 |

OTHER PUBLICATIONS

EPO Communication regarding extended European search report re Application No. 16177917.8-1568; Ref. EP106696GM, (Dec. 12, 2016) Dec. 2, 2016.

*Primary Examiner* — Hoi Lau
(74) *Attorney, Agent, or Firm* — Baker Botts L.L.P.

(57) ABSTRACT

An apparatus comprises a housing and a plurality of electrical contacts. Each of the plurality of electrical contacts are arranged to sequentially contact a contact device as the contact device moves through the housing. The contact device comprises a first end configured to couple to a bolt, a second end opposite the first end, and a conductive region between a first insulated region and a second insulated region.

19 Claims, 5 Drawing Sheets

(51) Int. Cl.
*G01D 5/25* (2006.01)
*G01B 7/004* (2006.01)
*G01B 7/04* (2006.01)
*G01B 7/02* (2006.01)
*G08B 21/18* (2006.01)

(56) References Cited

U.S. PATENT DOCUMENTS

| | | | | |
|---|---|---|---|---|
| 4,237,612 | A * | 12/1980 | Christian | G01B 3/20 33/784 |
| 6,265,973 | B1 * | 7/2001 | Brammall | B65D 90/00 340/539.1 |
| 2006/0032069 | A1 * | 2/2006 | Jensen | G01B 3/22 33/645 |
| 2009/0009328 | A1 * | 1/2009 | Brigham | G08B 13/06 340/568.4 |
| 2009/0091144 | A1 * | 4/2009 | Debrody | G09F 3/0317 292/327 |
| 2012/0176125 | A1 * | 7/2012 | Lee | B62J 99/00 324/207.25 |
| 2017/0016841 | A1 * | 1/2017 | Smith | G01B 7/02 |

* cited by examiner

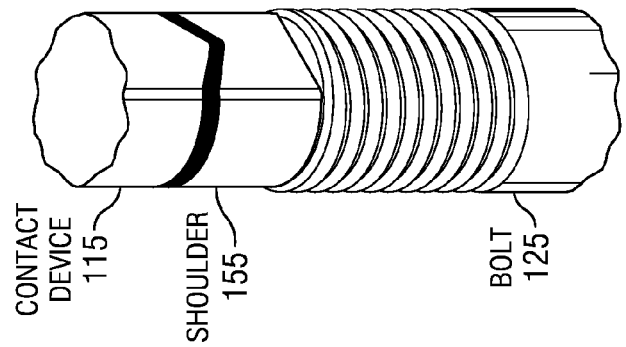
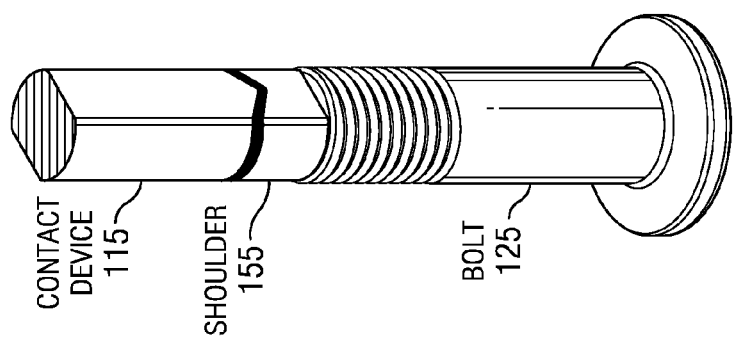
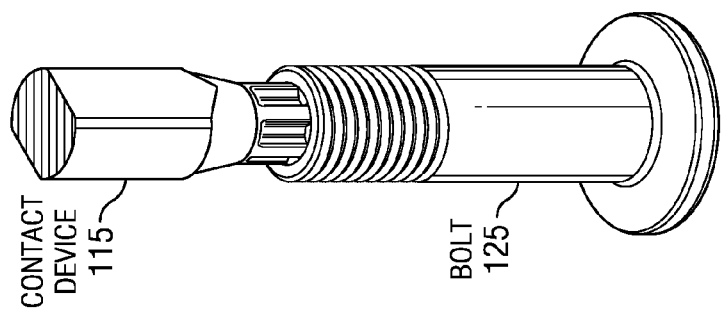
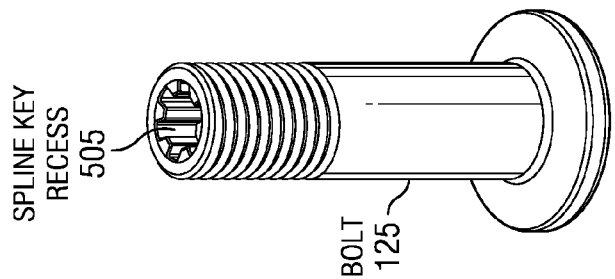

SYSTEM AND METHOD FOR THREAD PROTRUSION VERIFICATION

TECHNICAL FIELD

The present disclosure relates in general to fastening systems and, more particularly, to a system and method for verifying thread protrusion.

BACKGROUND

In the process of manufacturing aircraft or other vehicles and products, a large number of fasteners may be required to ensure proper operation of the finished product. In certain circumstances, various components may be required to meet certain specifications. For example, an amount of thread protrusion of a bolt may need to be verified. Verifying compliance with specifications can be time consuming and open to human error.

SUMMARY

According to embodiments of the present disclosure, disadvantages and problems associated with previous techniques for verifying an amount of thread protrusion may be reduced or eliminated.

In certain embodiments, a system comprising a contact device is disclosed. The contact device comprises a first end configured to couple to a bolt, a second end opposite the first end, and a conductive region between a first insulated region and a second insulated region. The system further comprises a unit for verifying an amount of thread protrusion of the bolt. The unit comprises a plurality of electrical brushes, each of the plurality of electrical brushes arranged to sequentially contact the contact device as the second end of the contact device moves through the unit. The plurality of electrical brushes comprises a power supply brush configured to apply an electrical current or voltage to the conductive region of the contact device; a first electrical brush configured to generate a first indication of the amount of thread protrusion of the bolt when the second end of the contact device has moved at least a first distance through the unit; a second electrical brush configured to generate a second indication of the amount of thread protrusion of the bolt when the second end of the contact device has moved at least a second distance through the unit; and a third electrical brush configured to generate a third indication of the amount of thread protrusion of the bolt when the second end of the contact device has moved at least a third distance through the unit.

Also disclosed is an apparatus. The apparatus comprises a housing and a plurality of electrical brushes, each of the plurality of electrical brushes arranged to sequentially contact a contact device as the contact device moves through the housing. The contact device comprises a first end configured to couple to a bolt, a second end opposite the first end, and a conductive region between a first insulated region and a second insulated region.

Also disclosed is a method. The method comprises coupling a first end of a contact device to a bolt, the contact device comprising a conductive region between a first insulated region and a second insulated region. The method further comprises fastening a nut to the bolt such that as the nut is fastened the contact device moves through a unit for verifying thread protrusion, the unit comprising a plurality of electrical brushes, each of the plurality of electrical brushes arranged to sequentially contact the contact device as the contact device moves through the unit. The method further comprises generating, by one or more of the plurality of electrical brushes, one or more indications of an amount of thread protrusion of the bolt from the nut.

Certain embodiments of the present disclosure may provide one or more technical advantages. As one example, verification of thread protrusion may be made at the same time that a nut is installed onto a bolt, advantageously eliminating the need for a mechanic to perform thread protrusion inspection after the nuts are installed and decreasing the potential that the mechanic will inadvertently miss some points of inspection. As another example, the thread protrusion verification mechanism may advantageously reduce the number of points that a quality inspector would need to recheck. As a further example, the risk associated with repairing nonconforming fastener installations may be advantageously minimized by identifying and reprocessing them as early as possible in the production process. As yet another example, no major modifications may need to be made to the fastening system to enable thread protrusion inspection to occur at the point of installation. Other advantages may be readily apparent to those having skill in the art. Certain embodiments may have none, some, or all of the recited advantages.

BRIEF DESCRIPTION OF THE DRAWINGS

For a more complete understanding of the disclosed embodiments and their features and advantages, reference is now made to the following description, taken in conjunction with the accompanying drawings, in which:

FIG. 5A illustrates an example bolt having a contact device recess, in accordance with certain embodiments;

FIG. 5B illustrates inconsistent penetration that may result when coupling the contact device to the bolt, in accordance with certain embodiments;

FIGS. 5C and 5D illustrate coupling of the contact device of FIG. 5B to the bolt using a shoulder, in accordance with certain embodiments.

DETAILED DESCRIPTION

Figure 1:
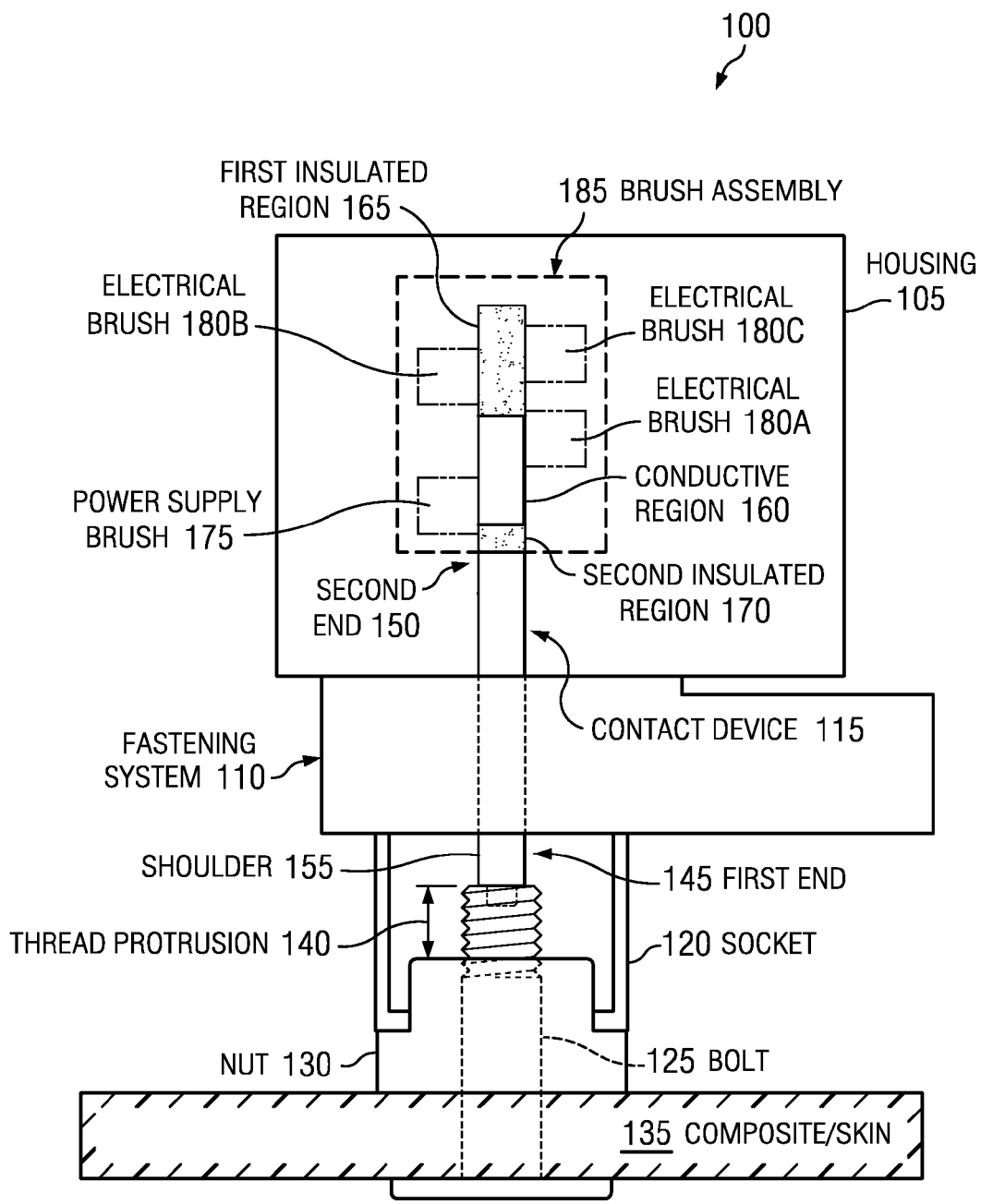
FIG. 1 illustrates a first view of a system for verifying thread protrusion, in accordance with certain embodiments.

As described above, in the process of manufacturing aircraft or other vehicles and products, a large number of fasteners may be required to ensure proper operation of the finished product. For example, aircraft manufacturing typically involves the installation of thousands of fasteners critical to the structural integrity and performance of the airframe, and has strict quality control requirements. Each fastener installation may have numerous quality control features that require visual and manual inspection to ensure compliance with engineering specifications. Various types of fasteners may be used to construct an aircraft or other vehicles and products. For example, in some instances the Alcoa EDDIE-BOLT fastening system may be used. In some cases, the EDDIE-BOLT installation process may require two separate thread protrusion inspections of 100% of the installed EDDIE-BOLTS. One inspection may be completed by the mechanic, and one may be completed by a quality inspector. Existing inspection methods may be very labor intensive; given the volume of fasteners involved, many hours may be spent conducting post-process inspection of fully compliant fastener installations on each aircraft.

Thread protrusion is one feature that may be inspected after each installation to ensure that the installed bolt was the correct length and/or to verify that a fastener is fully seated. Thread protrusion may be defined in any suitable manner, and the manner in which thread protrusion is defined may vary according to particular applications. For example, in certain embodiments thread protrusion may be defined as the length of a bolt pin protruding from the back side of a nut (i.e., the distance from the face of the nut to the top of the bolt pin that protrudes from the back side of the nut). Such a definition of thread protrusion may, for example, be appropriate in cases where the dimensions of the nuts used are known to be consistent within an acceptable tolerance range. As another example, thread protrusion may be defined as the distance from a composite or skin through which the bolt is inserted to the top of the bolt pin protruding through the back of the nut. Such a definition of thread protrusion may, for example, be appropriate in cases where the dimensions of the nuts used are not consistent.

An existing solution for verifying thread protrusion is to use a small step gauge. During inspection of an aircraft, for example, the small step gauge is placed against the aircraft surface adjacent to the installed bolt. The inspector then manually verifies that the length of the bolt pin protruding from the back side of the nut is within the appropriate portion of the gauge. In some cases, this is done manually to 100% of installed nuts by both the mechanic and the quality inspector. Such an approach may have certain deficiencies. For example, the process of manually verifying thread protrusion using a small step gauge is extremely time consuming and open to human error.

In certain embodiments, a thread protrusion verification mechanism is disclosed. In general, the thread protrusion verification mechanism utilizes movement of a contact device to measure thread protrusion. To do so, an electrical current or voltage may be applied to a conductive region of the contact device that is located between two insulated regions on either side of the conductive region. A plurality of electrical brushes may make contact with the contact device as the contact device moves. When the electrical brushes contact the conductive region of the contact device, the electrical brushes generate an indication of an amount of thread protrusion of the bolt pin from the installed nut. In certain embodiments, an added shoulder on the contact device helps maintain consistent bolt penetration. In certain embodiments, the brush assembly may be calibrated utilizing a calibration mechanism, such as, for example, two machine screws which mount the system into a housing.

The thread protrusion verification mechanism described herein may advantageously eliminate the need for a mechanic to manually perform a thread protrusion inspection using a step gauge after fasteners are installed, decreasing or eliminating the risk of the mechanic inadvertently missing some points of inspection. Furthermore, the thread protrusion verification mechanism may advantageously reduce the number of points that a quality inspector would need to recheck. The risk associated with repairing nonconforming fastener installations may be advantageously minimized by identifying and reprocessing them as early as possible in the production process. In some embodiments, no major modifications have to be made to an existing fastening tool, such as an EDDIE-BOLT wrench, to enable this inspection to occur at the point of installation.

FIG. 1 illustrates a first view of a system 100 for verifying thread protrusion, in accordance with certain embodiments. More particularly, system 100 for verifying thread protrusion includes a housing 105 coupled to a fastening system 110. Fastening system 110 may be any suitable fastening system. For example, fastening system 110 may be an EDDIE-BOLT wrench manufactured by Alcoa.

In some embodiments, fastening system 110 may include a contact device 115. Contact device 115 may be coupled to a socket 120, and contact device 115 may be configured to couple to a bolt 125. Bolt 125 may be configured to couple to a nut 130. Bolt 125 and nut 130 may be adapted to fasten structures. For example, bolt 125 and nut 130 may be used to fasten composite/skin 135. Composite/skin 135 may be any suitable surface. For example, in some embodiments composite/skin 135 may be the surface of an aircraft, vehicle, or any other suitable surface.

As nut 130 is screwed onto bolt 125, a portion of bolt 125 may protrude from the back of nut 130. This is shown in FIG. 1 as thread protrusion 140. The desired amount of thread protrusion 140 may vary according to particular applications or particular types of bolts 125 and nuts 130. An amount of thread protrusion 140 within an acceptable range may be necessary for verification that bolt 125 is the correct length and/or that the fastener is fully seated. The amount of thread protrusion 140 may increase as nut 130 is screwed further onto bolt 125. Although FIG. 1 illustrates thread protrusion 140 as the length of bolt 125 protruding from the back side of nut 130, in certain embodiments thread protrusion 140 may be a distance from composite/skin 135 to the top of bolt 125 protruding through the back of nut 130.

In certain embodiments, bolt 125 and nut 130 may be specially adapted to be coupled using a particular fastening system 110. For example, in certain embodiments bolt 125 and nut 130 may be components of the EDDIE-BOLT fastening system manufactured by Alcoa, and fastening system 110 may be one of a variety of EDDIE-BOLT wrenches. Although certain embodiments may be described in the context of the EDDIE-BOLT fastening system, the various embodiments described herein may be applicable to any other suitable fastening system with appropriate geometry modifications.

Figure 3:
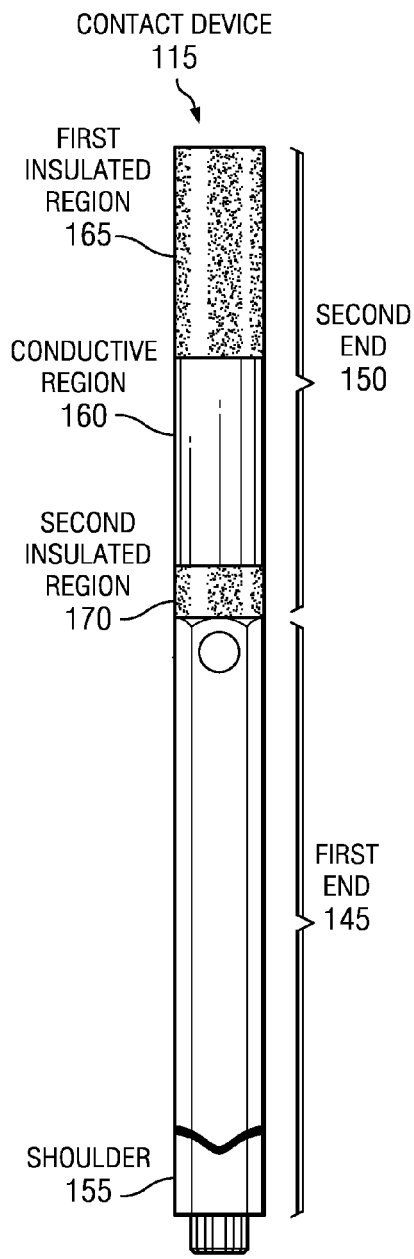
FIG. 3 illustrates an example contact device that may be used in the system for verifying thread protrusion shown in FIGS. 1 and 2, in accordance with certain embodiments.

As described above, fastening system 110 includes contact device 115. Contact device 115 may be made of any suitable material or combination of materials. In certain embodiments, contact device 115 may be a spline key used in the EDDIE-BOLT fastening system. Contact device 115 has a first end 145 and a second end 150 opposite first end 145. First end 145 of contact device 115 may be configured to couple to bolt 125. In certain embodiments, first end 145 of contact device 115 may prevent bolt 125 from rotating while fastening system 110 screws nut 130 onto bolt 125. In certain embodiments, first end 145 of contact device 115 may include a shoulder 155, as illustrated in FIGS. 3 and 5 below. Shoulder 155 may be configured to allow contact device 115 to sit at a fixed distance inside bolt 125. In other embodiments, contact device 115 may couple to bolt 125 in any suitable manner, and shoulder 155 may not be included.

In certain embodiments, second end 150 of contact device 115 includes a conductive region 160. Conductive region 160 may be configured to conduct an electrical current or voltage applied to conductive region 160. Conductive region 160 may be made of any suitable material or combination of materials that is electrically conductive. As one example, conductive region 160 may be made of copper. Conductive region 160 may be between a first insulated region 165 and a second insulated region 170. First insulated region 165 and second insulated region 170 may be formed from any suitable material that does not conduct an electrical current or voltage. For example, first insulated region 165 and second insulated region 170 may be formed of Ultra Electrical Insulating Rexolite Polystyrene.

Housing 105 may be coupled to fastening system 110 such that a portion of contact device 115 is positioned inside housing 105. Housing 105 may be coupled to fastening system 110 in any suitable manner. In certain embodiments, housing 105 may be removably coupled to fastening system 110. Housing 105 may be formed of any suitable material. As one example, housing 105 may be formed of plastic. Housing 105 may include any suitable components. For example, housing 105 may include a power supply brush 175 and a plurality of electrical brushes 180 (e.g., 180A-180C). In certain embodiments, power supply brush 175 and the plurality of electrical brushes 180 may be elements of a brush assembly 185. In certain embodiments, power supply brush 175 and the plurality of electrical brushes 180 may be individual components.

Power supply brush 175 and the plurality of electrical brushes 180 may be any appropriate electrical contacts. Power supply brush 175 and the plurality of electrical brushes 180 may be configured to contact contact device 115 as contact device 115 moves through housing 105 as fastening system 110 screws nut 130 onto bolt 125. Power supply brush 175 may be configured to apply an electrical current or voltage to conductive region 160. Power supply brush 175 and the plurality of electrical brushes 180 may be formed from any suitable materials. For example, in certain embodiments power supply brush 175 and the plurality of electrical brushes 180 may be direct current (DC) motor brushes formed from graphite. In certain embodiments, a shape of a portion of power supply brush 175 and the plurality of electrical brushes 180 may be curved. This may advantageously provide better contact between contact device 115 and power supply brush 175 and/or electrical brushes 180. Power supply brush 175 and electrical brushes 180 are described in more detail below in relation to FIG. 4.

In operation, fastening system 110 may be used to screw nut 130 onto bolt 125. As fastening system 110 screws nut 130 onto bolt 125, fastening system 110 and housing 105 may move toward the composite/skin 135 in which bolt 125 and nut 130 are being installed. The movement of fastening system 110 and housing 105 may cause contact device 115 to move through housing 105. In certain embodiments, power supply brush 175 may apply an electrical current or voltage to conductive region 160. As contact device 115 continues to move through housing 105 as nut 130 is screwed onto bolt 125, electrical brushes 180 may sequentially contact conductive region 160. That is, each of the plurality of electrical brushes 180 may contact conductive region 160 at different times as contact device 115 moves through housing 105 as fastening system 110 screws nut 130 onto bolt 125. For example, a first electrical brush 180A may contact conductive region 160 when second end 150 of contact device 115 has moved at least a first distance through housing 105, a second electrical brush 180B may contact conductive region 160 when second end 150 of contact device 115 has moved at least a second distance through housing 105, and a third electrical brush 180C may contact conductive region 160 when second end 150 of contact device 115 has moved at least a third distance through housing 105. Power supply brush 175 and electrical brushes 180 may move along contact device 115 at the same rate as nut 130 is being screwed onto bolt 125.

In certain embodiments, when an electrical brush 180 contacts conductive region 160 while power supply brush 175 is applying an electrical current or voltage to conductive region 160, electrical brush 180 may generate an indication of an amount of thread protrusion 140 of bolt 125 from the back of nut 130. The indication of an amount of thread protrusion 140 may be based on the position of contact device 115. For example, when one of the plurality of electrical brushes 180 contacts conductive region 160 while an electrical current or voltage is being applied by power supply brush 175, it may cause the electrical brush 180 contacting conductive region 160 of contact device 115 to send a message to the tool. For example, if in contact with conductive region 160 of contact device 115, each electrical brush 180 may translate the position of contact device 115 into an amount of thread protrusion 140. In certain embodiments, the signal from each electrical brush 180 may light up an LED light for a checkpoint (e.g., "too short", "correct", and "too long"). This design accurately captures the thread protrusion measurement using movement of contact device 115. In certain embodiments, the position of the plurality of electrical brushes 180, the length of conductive region 160, and the length of first insulated region 165 and second insulated region 170 may determine the regions associated with the various checkpoints (e.g., "too short", "correct", and "too long") and may be directly relatable to the thread protrusion measurement. This is described in more detail below in relation to FIG. 2.

Figure 2:
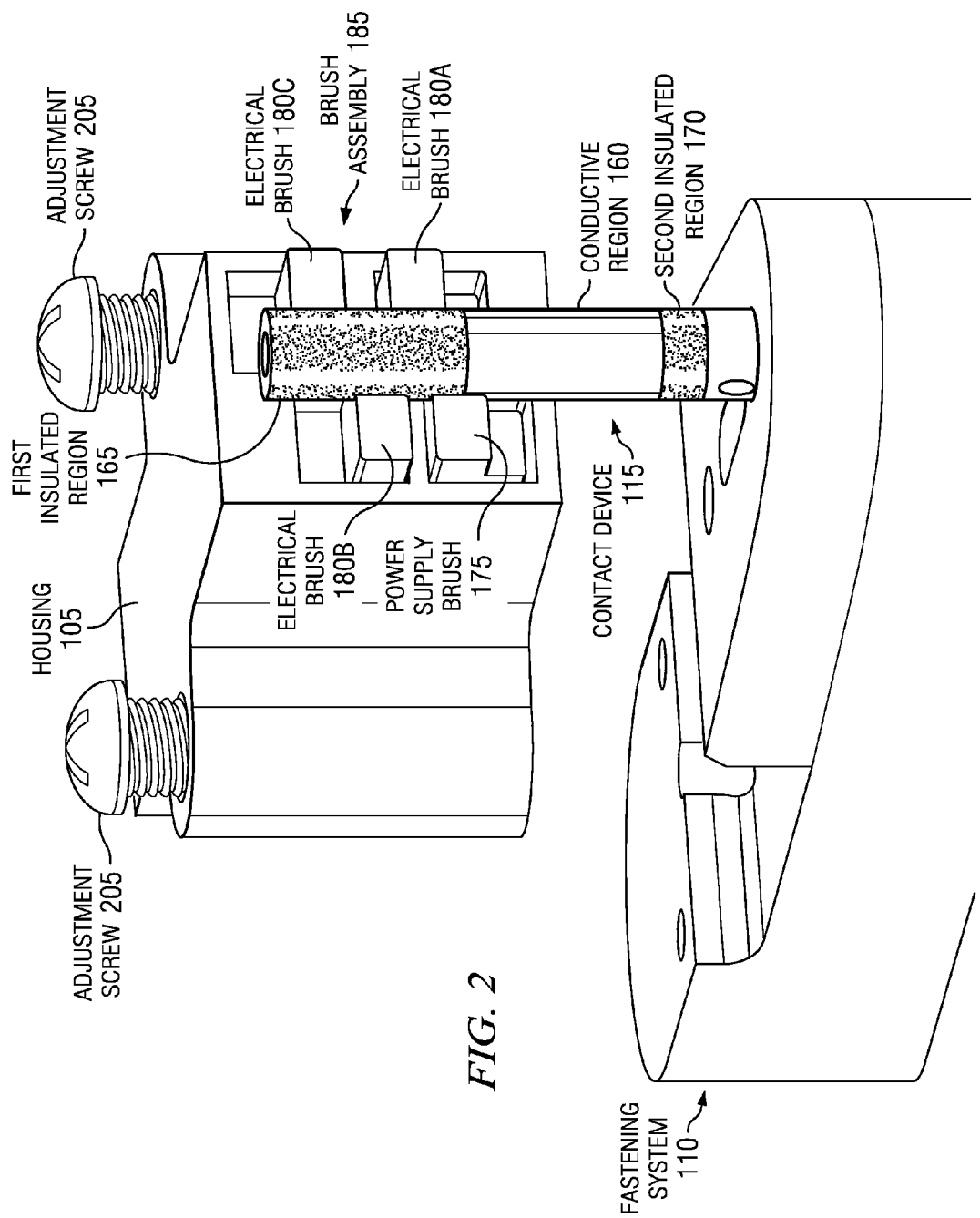
FIG. 2 illustrates a second view of a system for verifying thread protrusion, in accordance with certain embodiments.

FIG. 2 illustrates a second view of a system for verifying thread protrusion, in accordance with certain embodiments. As described above, housing 105 may be coupled to fastening system 110 such that housing 105 is positioned over a portion of contact device 115. Housing 105 may include a single power supply brush 175 and any appropriate number of electrical brushes 180. The illustrated embodiment of FIG. 2, for example, includes three electrical brushes: 180A, 180B, and 180C. Power supply brush 175 and electrical brushes 180A, 180B, and 180C may be configured to contact contact device 115. In some embodiments, power supply brush 175 and electrical brushes 180A, 180B, and 180C may be installed in brush assembly 185.

As described above, contact device 115 may include conductive region 160 between first insulated region 165 and second insulated region 170. As described above in relation to FIG. 1, as fastening system 110 screws nut 130 onto bolt 125, contact device 115 may move through housing 105. In certain embodiments, power supply brush 175 and electrical brushes 180A-C may be configured to sequentially contact conductive region 160 of contact device 115 as it moves through housing 105.

To illustrate, consider the following example. As described above, fastening system 110 may be used to screw nut 130 onto bolt 125. Prior to screwing nut 130 onto bolt 125, power supply brush 175 and electrical brushes 180 may be in contact with contact device 115 when contact device 115 is at rest in initial position. At such a time, any of the plurality of brushes may be in contact with first insulated region 165, creating an incomplete circuit.

As nut 130 is screwed down bolt 125 by fastening system 110, contact device 115 may move up through housing 105. As contact device 115 moves, power supply brush 175 may come into contact with conductive region 160. Power supply brush 175 may apply an electrical current or voltage to conductive region 160. As contact device 115 continues to move up through housing 105 while conductive region 160 is in contact with power supply brush 175, another electrical brush 180 may contact conductive region 160. For example, in the illustrated embodiment of FIG. 2, the next electrical brush 180 to contact conductive region 160 as nut 130 is screwed down bolt 125 will be electrical brush 180A.

Electrical brush 180A may make contact with conductive region 160 after contact device 115 moves at least a first distance through housing 105. At that point, only power supply brush 175 and electrical brush 180A may be in contact with conductive region 160. Electrical brushes 180B and 180C may at that point, for example, be in contact with first insulated region 165. Once in contact with conductive region 160 when power supply brush 175 is applying an electrical current or voltage, a first circuit may be completed, and a first indication of the amount of thread protrusion 140 of bolt 125 may be generated. For example, when electrical brush 180A comes into contact with conductive region 160, a first circuit may be completed that causes a first LED light to illuminate. The first LED light may provide a first indication of the amount of thread protrusion 140. For example, the first indication may comprise an indication that the amount of thread protrusion 140 is too short, or below an acceptable range. The acceptable range may be any suitable range. For example, it may be a range of acceptable thread protrusion for the particular type of bolt being used, and may vary according to particular applications.

As fastening system 110 continues to screw nut 130 down bolt 125, contact device 115 may continue to move up through housing 105. After moving at least a second distance through housing 105, electrical brush 180B may make contact with conductive region 160. While in contact with conductive region 160 when power supply brush 175 is applying an electrical current or voltage, electrical brush 180B may generate a second indication of the amount of thread protrusion 140 of bolt 125. For example, in certain embodiments, when electrical brush 180B comes into contact with conductive region 160, a second circuit may be completed that causes a second LED light to illuminate. The second LED light may provide a second indication of the amount of thread protrusion 140. For example, when electrical brush 180B is in contact with conductive region 160, the second indication may comprise an indication that the amount of thread protrusion 140 is within an acceptable range. As described above, the acceptable range may be any suitable range, and may vary according to particular applications.

As fastening system 110 continues to screw nut 130 down bolt 125, contact device 115 may continue to move further up through housing 105. After moving at least a third distance through housing 105, electrical brush 180C may make contact with conductive region 160. While in contact with conductive region 160 when power supply brush 175 is applying an electrical current or voltage, electrical brush 180C may generate a third indication of the amount of thread protrusion 140 of bolt 125. For example, when electrical brush 180C contacts conductive region 160, a third circuit may be completed that causes a third LED light to illuminate. The third LED may provide a third indication of the amount of thread protrusion 140. For example, when electrical brush 180C is in contact with conductive region 160, the third indication may be an indication that the amount of thread protrusion 140 is too long, or above the acceptable range. As described above, the acceptable range may be any suitable range, and may vary according to particular applications.

The size of bolts 125 and nuts 130 used by fastening system 110 may vary according to particular applications. For example, in some cases a particular bolt 125 may be longer than another bolt 125 previously installed using fastening system 110. A longer bolt 125 may change the initial position of contact device 115 relative to power supply brush 175 and electrical brushes 180. In such cases, the indications generated by electrical brushes 180A-C may not be accurate representations of the amount of thread protrusion. To address this problem, certain embodiments of housing 105 may include a calibration mechanism. The calibration mechanism may be used to adjust the height of brush assembly 185 relative to contact device 115. The calibration mechanism may be any suitable mechanism for adjusting the height of brush assembly 185 and/or power supply brush 175 and plurality of electrical brushes 180. In certain embodiments, and as illustrated in FIG. 2, the calibration mechanism may include one or more adjustment screws 205. Adjustment screws 205 may be configured to raise and lower the height of brush assembly 185 with respect to fastening system 110 as adjustment screws 205 are turned. The present disclosure contemplates that any suitable number of adjustment screws 205 (or other suitable calibration mechanism) may be used, and adjustment screws 205 (or other suitable calibration mechanism) may be located in any suitable position. Moreover, adjustment screws 205 may be manual and/or motor-driven. Although FIG. 2 illustrates the calibration mechanism using adjustment screws 205, the present disclosure contemplates that the calibration mechanism may be any suitable mechanism to raise and/or lower housing 105 relative to fastening system 110.

Although FIG. 2 illustrates a particular configuration of system for verifying thread protrusion 100, the present disclosure is not limited to the particular configuration illustrated in FIG. 2. For example, in certain embodiments the first, second, and third circuits described above may not be discrete circuits, but rather connected to a processor or application-specific integrated circuit (ASIC). As another example, the present disclosure contemplates that the one or more generated indications of an amount of thread protrusion 140 described above may be configured in any suitable manner. In some embodiments, one or more of the first, second, and third LEDs may remain illuminated as contact device 115 moves through housing 105. In some embodiments, one or more of the first, second, and third LEDs may turn off when a subsequent electrical brush 180 contacts conductive region 160. To illustrate, consider the following example. As described above, when electrical brush 180A comes into contact with conductive region 160, a first circuit may be completed that causes a first LED to illuminate. When electrical brush 180B comes into contact with conductive region 160, a second circuit may be completed that causes a second LED to illuminate. In some embodiments, the first LED may remain illuminated, such that the first LED and second LED are illuminated at the same time. In some embodiments, the first LED may turn off when the second circuit is completed, such that only one of the LEDs is on at any given time. Other variations are possible, and the present disclosure contemplates that the indications of the amount of thread protrusion 140 may be generated in any suitable manner.

Although certain embodiments describe the use of LEDs, the present disclosure contemplates that the indications of the amount of thread protrusion 140 may be generated in any suitable manner, and may use any suitable combination of hardware and/or software. For example, system for verifying thread protrusion 100 may include a display, such as an LCD, LED, or any other suitable display. The display may include any appropriate circuitry and hardware configured to present signals on the display. As another example, the indications of the amount of thread protrusion 140 may be generated using any suitable physical indication, such as sound and/or vibration.

System for verifying thread protrusion 100 may be advantageous in that it may eliminate the need for a user, such as a mechanic, to manually perform a typical thread protrusion inspection after nuts 130 are installed. Instead, the installer may verify that there is a proper amount of thread protrusion 140 of bolt 125 from nut 130 while nut 130 is screwed onto bolt 125 based on the one or more indications generated by electrical brushes 180A-C, as described above. Furthermore, the installer may advantageously be made aware of nonconforming fastener installations as early as possible, which may reduce the risk associated with repairing nonconforming fastener installations.

Although the system illustrated in FIG. 2 illustrates a particular configuration of a system for verifying thread protrusion 100, the present disclosure contemplates that other embodiments may use different configurations. For example, the present disclosure contemplates that any suitable number and any suitable configuration of electrical brushes 180 may be used. Furthermore, although the example illustrated in FIG. 2 describes the indications of an amount of thread protrusion generated by the various electrical brushes 180, the present disclosure contemplates that any suitable mechanism of generating an indication of the amount of thread protrusion based on the movement of contact device 115 may be used. In certain embodiments, and as described above, the first, second, and third indications may be considered as checkpoints, and an illuminated LED may indicate when each checkpoint is reached, i.e., a first checkpoint ("too short"), a second checkpoint ("correct"), and a third checkpoint ("too long"). In some embodiments, other means of indicating the amount of thread protrusion 140 may be used. For example, electrical brushes 180 may generate one or more outputs to a computer processor, which may then generate one or more suitable indications indicating an amount of thread protrusion 140 based the movement of contact device 115.

FIG. 3 illustrates an example contact device 115 that may be used in the system for verifying thread protrusion 100 illustrated in FIGS. 1 and 2, in accordance with certain embodiments. Contact device 115 may be formed from any suitable material or combination of materials, and may have any suitable dimensions. As described above, contact device 115 may include first end 145 and second end 150. First end 145 of contact device 115 may be configured to couple to bolt 125. In certain embodiments, contact device 115 may include a shoulder 155. Shoulder 155 may be located proximate to first end 145. In certain embodiments, shoulder 155 is configured to allow consistent penetration of contact device 115 within bolt 125. Shoulder 155 is described in more detail below in relation to FIGS. 5A-D.

In some embodiments, contact device 115 includes conductive region 160 between first insulated region 165 and second insulated region 170. In certain embodiments, conductive region 160, first insulated region 165, and second insulated region 170 may be located near or at second end 150. Conductive region 160 may have any suitable dimensions. The dimension of conductive region 160 may vary according to particular applications. Conductive region 160 may be formed of any suitable material. For example, in certain embodiments conductive region 160 may be formed of copper, or any other suitable conductive material.

First insulated region 165 and second insulated region 170 may be located on either side of conductive region 160. First insulated region 165 and second insulated region 170 may have any suitable dimensions. In certain embodiments, first insulated region 165 and second insulated region 170 may be the same size. In certain other embodiments, and as illustrated in FIG. 3, the size of first insulated region 165 may be different than the size of second insulated region 170. First insulated region 165 may be made from the same or different materials as second insulated region 170. First insulated region 165 and second insulated region 170 may be made of any suitable material or combination of materials that do not conduct electricity. For example, first insulated region 165 and second insulated region 170 may be made of Ultra Electrical Insulating Rexolite Polystyrene.

Figure 4:
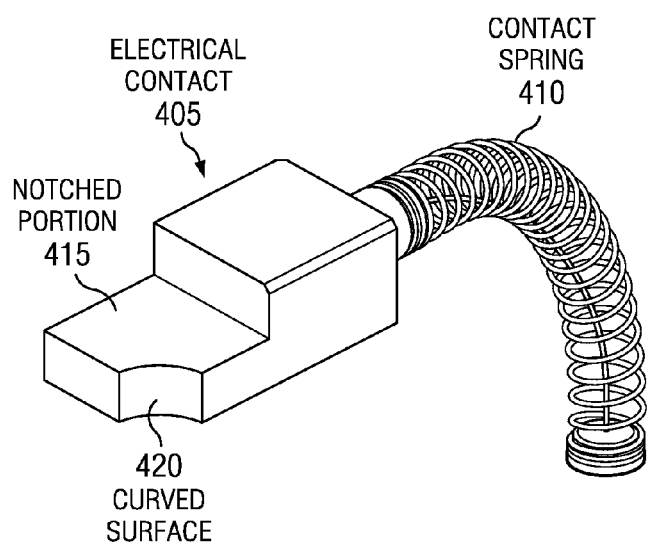
FIG. 4 illustrates an example power supply brush or electrical brush that may be used in the system for verifying thread protrusion shown in FIGS. 1 and 2, in accordance with certain embodiments.

FIG. 4 illustrates an example power supply brush 175 or electrical brush 180 that may be used in the system for verifying thread protrusion 100 illustrated in FIGS. 1 and 2, in accordance with certain embodiments. Power supply brush 175 or electrical brush 180 may include an electrical contactor 405 and a contact spring 410. Contact spring 410 may ensure that electrical contactor 405 maintains constant contact with contact device 115.

Electrical contactor 405 may be formed of any suitable material or combination of materials that conduct electricity. In certain embodiments, electrical contactor 405 may be formed of graphite. In some embodiments, electrical contactor 405 may include a notched portion 415. Notched portion 415 may have a curved surface 420 for contacting contact device 115. In certain embodiments, notched portion 415 may allow for a tolerance range. The tolerance range may be any suitable amount, and may vary according to particular applications.

FIG. 5A illustrates an example bolt 125 having a contact device recess 505, in accordance with certain embodiments. As described above, contact device 115 may be configured to couple to an end of bolt 125. In certain embodiments, contact device 115 may be configured to couple to bolt 125 at contact device recess 505.

FIG. 5B illustrates inconsistent penetration that may result when coupling contact device 115 to bolt 125, in accordance with certain embodiments. As illustrated in FIG. 5B, there may be inconsistent penetration of contact device recess 505 by contact device 115. This may be caused, for example, by inconsistent machining of these pieces across fastening systems. Inconsistent penetration of contact device recess 505 by contact device 115 may be problematic in that it may result in inconsistent distances between the end of bolt 125 and conductive region 160 of contact device 115, as described above. Inconsistent distances between the end of bolt 125 and conductive region 160 of contact device 115 may result in inconsistent measurements of the amount of thread protrusion 140 from one measurement to the next.

FIGS. 5C and 5D illustrate coupling of contact device 115 of FIG. 5B to bolt 125 using shoulder 155, in accordance with certain embodiments. To address the problem of inconsistent penetration and other problems, certain embodiments of contact device 115 may include shoulder 155. As illustrated in FIGS. 5C and 5D, shoulder 155 provides for consistent penetration of bolt 125 by contact device 115, allowing contact device 115 to sit at a fixed distance inside the end of bolt 125. As a result, the distance between the end of bolt 125 and conductive region 160 of contact device 115 is consistent across measurements, advantageously allowing consistent measurements of an amount of thread protrusion 140 from measurement to measurement.

Although FIGS. 4 and 5A-5D describe a particular example configuration of contact device 115, the present disclosure contemplates that any suitable contact device 115 may be used. In certain embodiments, the manner in which contact device 115 couples to bolt 125 may vary according to the type of fastener with which system for verifying thread protrusion 100 is used. For example, contact device 115 may couple to bolt 125 in any suitable manner, such as by touching off the surface of bolt 125 instead of coupling to bolt 125 via contact device recess 505, as shown in FIGS. 5A-5D. As another example, in certain embodiments contact device 115 and shoulder 155 may be combined such that contact device 115 and shoulder 155 comprise a single piece. In other embodiments, contact device 115 and shoulder 155 may be separate pieces, and shoulder 155 may be used only when appropriate (e.g., when bolt 125 includes a contact device recess 505 that may be inconsistently machined). In certain embodiments, contact device 115 may not include shoulder 155.

Figure 6:
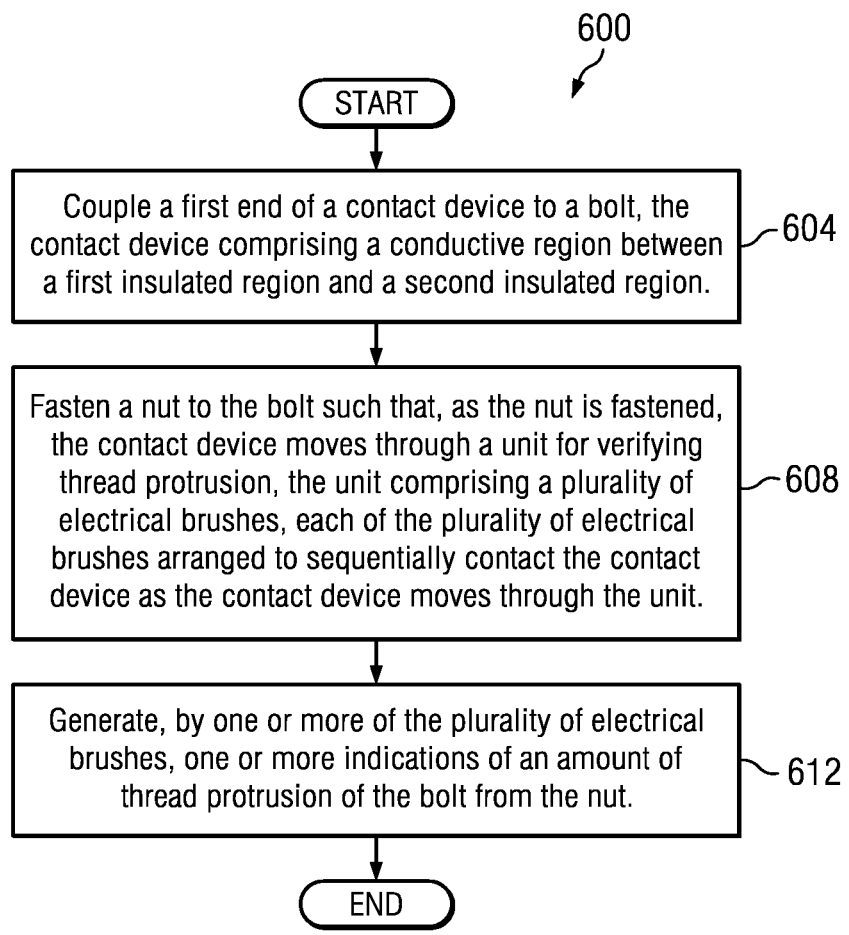
FIG. 6 illustrates a method for verifying thread protrusion, in accordance with certain embodiments.

FIG. 6 illustrates a method 600 for verifying thread protrusion, in accordance with certain embodiments. Method 600 begins at step 604, when a first end of a contact device is coupled to a bolt, the contact device comprising a conductive region between a first insulated region and a second insulated region. The contact device may be a component of a fastening system, such as, for example, an EDDIE-BOLT fastening system. In certain embodiments, the bolt may also be a component of the fastening system.

At step 608, a nut is fastened to the bolt such that as the nut is fastened, the contact device moves through a unit for verifying thread protrusion. The unit comprises a plurality of electrical brushes, each of the plurality of electrical brushes arranged to sequentially contact the contact device as the contact device moves through the unit. The plurality of electrical brushes may be graphite DC motor brushes. In certain embodiments, the plurality of electrical brushes comprise a power supply brush, and method 600 further comprises applying, by the power supply brush, an electrical current or voltage to the conductive region of the contact device.

At step 608, one or more of the plurality of electrical brushes generates one or more indications of an amount of thread protrusion of the bolt from the nut. In certain embodiments, the plurality of electrical brushes comprise a first electrical brush, a second electrical brush, and a third electrical brush. The first electrical brush may generate a first indication of the amount of thread protrusion of the bolt when the first electrical brush contacts the conductive region of the contact device after the contact device has moved at least a first distance through the unit. The second electrical brush may generate a second indication of the amount of thread protrusion of the bolt when the second electrical brush contacts the conductive region of the contact device after the contact device has moved at least a second distance through the unit. The third electrical brush may generate a third indication of the amount of thread protrusion of the bolt after the third electrical brush contacts the conductive region of the contact device when the contact device has moved at least a third distance through the unit. In certain embodiments, the first indication may comprise an indication that an amount of thread protrusion of the bolt is below the acceptable range, the second indication may comprise an indication that the amount of thread protrusion of the bolt is within the acceptable range, and the third indication may comprise an indication that the amount of thread protrusion of the bolt is above the acceptable range.

In certain embodiments, one or more of the one or more generated indications may be displayed. For example, one or more of the one or more generated indications may be displayed using an LED, an LCD, or any other suitable display. As another example, one or more of the generated indications may be done using any suitable physical indication, such as sound or vibration. The method may further comprise adjusting a position of the unit for verifying thread protrusion relative to the contact device. For example, a calibration mechanism may be used to adjust the position of the brush assembly and/or power supply brush and plurality of electrical brushes.

Modifications, additions, or omissions may be made to the systems and apparatuses described herein without departing from the scope of the disclosure. The components of the systems and apparatuses may be integrated or separated. Moreover, the operations of the systems and apparatuses may be performed by more, fewer, or other components. Additionally, operations of the systems and apparatuses may be performed using any suitable logic comprising software, hardware, and/or other logic. As used in this document, "each" refers to each member of a set or each member of a subset of a set.

Modifications, additions, or omissions may be made to the methods described herein without departing from the scope of the disclosure. The methods may include more, fewer, or other steps. Additionally, steps may be performed in any suitable order.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

The invention claimed is:

1. A system, comprising:
   a contact device comprising:
      a first end configured to couple to a bolt;
      a second end opposite the first end; and
      a conductive region between a first insulated region and a second insulated region; and
   a unit for verifying an amount of thread protrusion of the bolt, the unit comprising a plurality of electrical brushes, each of the plurality of electrical brushes arranged to sequentially contact the contact device as the second end of the contact device moves through the unit, wherein the plurality of electrical brushes comprises:
      a power supply brush configured to apply an electrical current or voltage to the conductive region of the contact device;
      a first electrical brush configured to generate a first indication of the amount of thread protrusion of the bolt when the second end of the contact device has moved at least a first distance through the unit;
      a second electrical brush configured to generate a second indication of the amount of thread protrusion of the bolt when the second end of the contact device has moved at least a second distance through the unit; and
      a third electrical brush configured to generate a third indication of the amount of thread protrusion of the bolt when the second end of the contact device has moved at least a third distance through the unit.

2. The system of claim 1, wherein:
the first electrical brush is configured to generate the first indication of the amount of thread protrusion of the bolt when the first electrical brush contacts the conductive region of the contact device;
the second electrical brush is configured to generate the second indication of the amount of thread protrusion of the bolt when the second electrical brush contacts the conductive region of the contact device; and
the third electrical brush is configured to generate the third indication of the amount of thread protrusion of the bolt when the third electrical brush contacts the conductive region of the contact device.

3. The system of claim 1, wherein:
the first indication comprises an indication that the amount of thread protrusion of the bolt is below an acceptable range;
the second indication comprises an indication that the amount of thread protrusion of the bolt is within the acceptable range; and
the third indication comprises an indication that the amount of thread protrusion of the bolt is above the acceptable range.

4. The system of claim 1, wherein the unit for verifying thread protrusion further comprises a display for providing one or more of the one or more generated indications to a user.

5. The system of claim 1, wherein the contact device further comprises a shoulder proximate to the first end and configured to allow the contact device to sit at a fixed distance inside the bolt.

6. The system of claim 1, further comprising a calibration mechanism for adjusting a position of the unit for verifying thread protrusion relative to the contact device.

7. The system of claim 1, wherein the electrical brushes comprise graphite direct current motor brushes.

8. An apparatus, comprising:
a housing;
a plurality of electrical contacts, each of the plurality of electrical contacts arranged to sequentially contact a contact device as the contact device moves through the housing, the contact device comprising:
a first end configured to couple to a bolt;
a second end opposite the first end; and
a conductive region between a first insulated region and a second insulated region; and
a calibration mechanism for adjusting a position of the apparatus relative to the contact device.

9. The apparatus of claim 8, wherein the plurality of electrical contacts comprise:
a power supply contact configured to apply an electrical current or voltage to the conductive region of the contact device;
a first electrical contact configured to generate a first indication of an amount of thread protrusion of the bolt when the second end of the contact device has moved at least a first distance through the unit;
a second electrical contact configured to generate a second indication of the amount of thread protrusion of the bolt when the second end of the contact device has moved at least a second distance through the unit;
a third electrical contact configured to generate a third indication of the amount of thread protrusion of the bolt from the nut when the second end of the contact device has moved at least a first distance through the unit.

10. The apparatus of claim 9, wherein:
the first indication comprises an indication that the amount of thread protrusion of the bolt is below an acceptable range;
the second indication comprises an indication that the amount of thread protrusion of the bolt is within the acceptable range; and
the third indication comprises an indication that the amount of thread protrusion of the bolt is above the acceptable range.

11. The apparatus of claim 9, further comprising a display for providing one or more of the one or more generated indications to a user.

12. The apparatus of claim 8, wherein the plurality of electrical contacts comprise graphite direct current motor brushes.

13. A method, comprising:
coupling a first end of a contact device to a bolt, the contact device comprising a conductive region between a first insulated region and a second insulated region;
fastening a nut to the bolt such that, as the nut is fastened, the contact device moves through a unit for verifying thread protrusion, the unit comprising a plurality of electrical brushes, each of the plurality of electrical brushes arranged to sequentially contact the contact device as the contact device moves through the unit; and
generating, by one or more of the plurality of electrical brushes, one or more indications of an amount of thread protrusion of the bolt from the nut.

14. The method of claim 13, wherein the plurality of electrical brushes comprises a power supply brush, and the method further comprises:
applying, by the power supply brush, an electrical current or voltage to the conductive region of the contact device.

15. The method of claim 13, wherein:
the plurality of electrical brushes comprises a first electrical brush, a second electrical brush, and a third electrical brush; and
generating, by one or more of the plurality of electrical brushes, one or more indications of an amount of thread protrusion of the bolt from the nut comprises one or more of:
generating, by the first electrical brush, a first indication of the amount of thread protrusion of the bolt when the first electrical brush contacts the conductive region of the contact device when the contact device has moved at least a first distance through the unit;
generating, by the second electrical brush, a second indication of the amount of thread protrusion of the bolt when the second electrical brush contacts the conductive region of the contact device when the contact device has moved at least a second distance through the unit;
generating, by the third electrical brush, a third indication of the amount of thread protrusion of the bolt when the third electrical brush contacts the conductive region of the contact device when the contact device has moved at least a third distance through the unit.

16. The method of claim 15, wherein:
the first indication comprises an indication that the amount of thread protrusion of the bolt is below an acceptable range;
the second indication comprises an indication that the amount of thread protrusion of the bolt is within the acceptable range; and the third indication comprises an indication that the amount of thread protrusion of the bolt is above the acceptable range.

17. The method of claim 13, further comprising displaying one or more of the one or more generated indications.

18. The method of claim 13, further comprising adjusting a position of the unit for verifying thread protrusion relative to the contact device.

19. The method of claim 13, wherein the plurality of electrical brushes comprises graphite direct current motor brushes.

* * * * *